United States Patent [19]

Curth et al.

[11] 4,416,018
[45] Nov. 15, 1983

[54] DEVICE FOR FORMING IMAGES OF LAYERS OF A THREE-DIMENSIONAL OBJECT BY SUPERPOSITION ZONOGRAMS

[75] Inventors: Claus P. Curth, Wilhelmshausen; Ulf Tiemens, Prisdorf; Erhard Klotz, Halstenbek, all of Fed. Rep. of Germany

[73] Assignee: U.S. Philips Corporation, New York, N.Y.

[21] Appl. No.: 237,302

[22] Filed: Feb. 23, 1981

[30] Foreign Application Priority Data

Feb. 23, 1980 [DE] Fed. Rep. of Germany ....... 3006828

[51] Int. Cl.³ ............................................. G03B 41/16
[52] U.S. Cl. .......................................... 378/2; 378/23
[58] Field of Search .......................... 378/2, 23, 25, 26

[56] References Cited

U.S. PATENT DOCUMENTS 4,023,037  5/1977  Weiss et al. .......................... 250/313

FOREIGN PATENT DOCUMENTS 1572421  7/1980  United Kingdom .................... 378/2

Primary Examiner—Craig E. Church
Attorney, Agent, or Firm—Marc D. Schechter

[57] ABSTRACT

The invention relates to a device for the imaging layers of a three-dimensional object. The device comprises a group of radiation sources which are situated in a common radiation source plane in order to irradiate an object arranged on an examination table. The drive also comprises a record carrier situated underneath the object for recording a source-distribution encoded image of the object. The encoded image consists of respective perspective images. The radiation source group and the record carrier are arranged to slide in opposite directions in parallel planes relative to the stationary object during a radiographic recording. Each of the connecting lines between the radiation sources and the center of the record carrier, pass through a corresponding fixed point in the object for all positions of the radiation source group.

12 Claims, 3 Drawing Figures

DEVICE FOR FORMING IMAGES OF LAYERS OF A THREE-DIMENSIONAL OBJECT BY SUPERPOSITION ZONOGRAMS

BACKGROUND OF THE INVENTION

The invention relates to a device for imaging layers of a three-dimensional object. The device includes a radiation source arranged to irradiate an object under examination with penetrating radiation from each of a plurality of source positions which are distributed in a common radiation source plane. The device also includes an examination table on which the object is arranged, and a record carrier which is situated underneath the object to record an encoded composite image of the object. The encoded image consists of a plurality of perspective images (corresponding to each source position) which can overlap one another.

A device of the kind described above is known from German Offenlegungsschrift No. 26 05 497. In this device, an object is irradiated from different perspective directions by means of a multiple radiation source which consists of several separate radiation sources which are situated in one plane. A source distribution encoded composite image of the object is recorded on a record carrier which is arranged underneath the object. The composite image can subsequently be decoded in order to form images of layers of the object, for example, by the decoding method described in German Offenlegungsschrift No. 24 14 322.

However, the formation of the encoded images by means of the device of Offenlegungsschrift No. 2605497 has the drawback in that the superposed imaging of central projections from different perspectives causes superposition artefacts in the decoded image. Such artifacts are due to object structures, for example bones, which are not situated in the region of interest in the selected sectional layer of the object. As a consequence the quality of a decoded sectional layer image is reduced.

It is also a drawback that all superposed central projections are imaged with a comparatively large contrast range. As a result, in the film region which is strongly exposed by a central projection, object information which is projected on the same film region from other perspectives is lost. The contrast range of a layer image or zonogram is essentially smaller than that of a central projection.

SUMMARY OF THE INVENTION

It is an object of the invention to provide a device for forming layer images by means of which artefacts, in the decoded layer image, which are caused by object details situated outside the reconstructed object layer are reduced.

This object is achieved by arranging the radiation source group and the record carrier to slide in opposite directions in mutually parallel planes relative to the stationary object during a radiographic exposure, so that a straight line connecting a radiation source position to the center of the record carrier, will pass through a corresponding fixed point in a common plane through the object for all radiation source means positions.

The object of the invention can alternatively be achieved by moving the object and the record carrier in the same direction (with respect to the stationary radiation source means) in planes parallel to the radiation source plane during a radiographic exposure, so that a straight line connecting a radiation source position to the center of the record carrier will pass through a corresponding fixed point relative to and in a common plane through the object for all radiation source positions and for all object positions.

Thus, during the recording of a source-distribution encoded composite image by means of a device according to the invention, only a predetermined zonographic region, for example a sectional layer region having a thickness of from a few millimeters to a few centimeters, of the irradiated object will be sharply imaged. All object details situated outside this sectional layer region will be recorded in a blurred manner. The formation of artefacts in the decoded image due to object structures situated outside the relevant object layer will thus be greatly reduced. Any one of a plurality of spaced layer images of the object located in a sharply imaged layer region can then be decoded from the composite image relating to that region by means of the known decoding method.

The image contrast of the decoded layer will be good because object details which are situated outside the object layer will have been blurred during the zonographic exposure. Moreover, they will have little effect on the formation of the layer image during the decoding process. In principles, two blurring operations are carried out on object details which do not belong to the selected object layer: the first blurring operation is carried out during the zonographic recording exposure, and the second blurring operation is carried out during the decoding process. The contrast is thus enhanced.

The recording of superposed zonograms offers further advantages in that (1) the film is not unnecessarily blackened by object structures which are not situated in the region of interest, and (2) for the actual object information, a film having a smaller contrast range can be used.

In a preferred embodiment according to the invention, the record carrier is a multiplefilm cassette for simultaneously recording images of a plurality of layer regions of the object which are situated one beneath the other, so that several layer regions of the object can be made available for decoding as a result of only one recording operation.

A device according to the invention can be used, for example, for bone tomography. The device can also be used advantageously for selective layer examinations, for example of the auditory canals, the orbits or the vertebral column (i.e. objects where the desired depth can be imaged with few adjacently arranged zonographic object ranges).

DESCRIPTION OF THE PREFERRED EMBODIMENTS

Figures 1, 2:
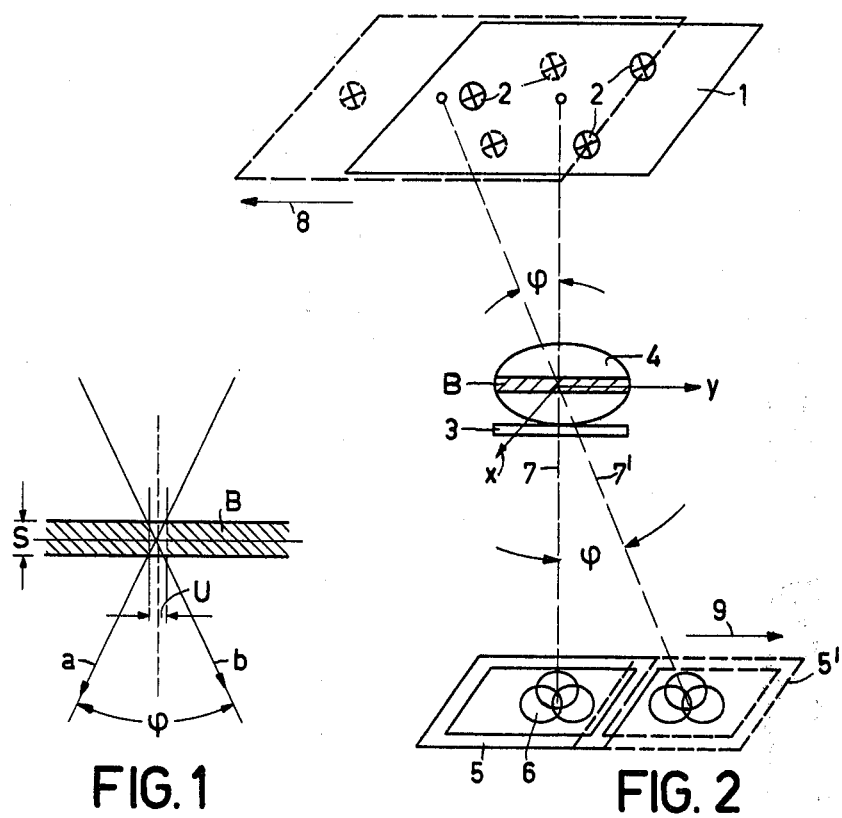
FIG. 1 schematically illustrates the layer thickness imaged by a zonogram.
FIG. 2 schematically shows a tomography apparatus according to the invention for forming zonographic layer images.

FIG. 1 is a sketch illustrating the layer thickness imaged by a zonogram. The layer thickness S is dependent on the layer angle φ between two lines a and b which denote, for example, the central rays of the radiation beam of a displaceable radiation source. The layer thickness S is also dependent on the permissible overall unsharpness U which can be allowed for the relevant field of application. All object details which are present within the shaded zone B during the recording of the zonogram will be sharply imaged. The degree of sharpness of the image will depend on the total unsharpness U which results from the layer angle φ and the layer thickness S. All object structures which are situated above and below the shaded zone B will be imaged with a greater degree of unsharpness, in other words in a blurred manner. Consequently artefacts caused by object structures outside of zone B will be substantially reduced.

FIG. 2 shows a tomography apparatus according to the invention for forming zonographic layer images. The apparatus comprises a source assembly formed by a plurality or radiation sources 2 which are distributed in a common radiation source plane 1 according to a predetermined point distribution (see, for example, German Offenlegungsschrift No. 28 30 186). The number of radiation sources (X-ray tubes) may be, for example, 15 or more. For the sake of clarity, FIG. 2 shows only three radiation sources. It should be noted that, as an alternative, a single radiation source can be located in succession at the various source positions for irradiating the object.

Underneath the radiation sources 2, an object 4 is arranged on an examination table 3. Object 4 is irradiated by the distribution of radiation sources 2 so that the corresponding perspective images of the object 4 are superposed as a source-distribution encoded composite image 6 on a record carrier 5, for example an X-ray film, which is arranged underneath the object 4. The direction from which the radiation sources 2 irradiate the object 4 may extend, for example, along a line 7 which extends perpendicular to the zone B of the object 4, the radiation source plane 1 and the flat record carrier 5.

The assembly of radiation sources 2, which are housed for example in a common housing in order to form a multiple radiation source, and the record carrier 5, are each arranged to be slidable in their respective planes. In order to form a zonographic image of the object 4 during a radiographic exposure, the radiation sources 2 and the record carrier 5 are displaced in opposite directions 8 and 9 in their respective planes, while maintaining the respective planes at a constant separation. Along a line 7' connecting, for example, the centers of sources 2 and carrier 5, the straight paths subtend the same angle φ at the center of object 4 with respect to the first irradiation direction 7, so that the object 4 is irradiated in irradiation direction 7'. The point of intersection of the irradiation directions 7 and 7' is situated inside the object zone B.

Thus, sources 2 and carrier 5 are each slid so that a straight line connecting any radiation source to the center of the record carrier 5 will always pass through a corresponding fixed point (object point) in a common plane (X, Y) through the object 4, for all positions of the radiation source assembly relative to the stationary object. In carrying out this method, the individual radiation sources 2, while remaining at their respective locations in the source assembly, are tilted so that their radiation beams are always directed at the object 4. The radiation sources 2 can be continuously activated along their blurring path or can be briefly energized at successive positions therealong.

It will be apparent that instead of sliding the radiation source group 2 and the record carrier 5, the object 4 and the record carrier 5 can be slid in the same direction, subject to the constraints described above, parallel to the stationary radiation source assembly 2. The individual radiation beams then remain directed onto the object.

A further possibility for forming zonographic images in a device according to the invention comprises displacing the radiation source group 2 and the record carrier 5 in their parallel planes along corresponding circular paths in opposite directions. For example, the line 7 which extends perpendicular to the layer plane B would then pass through the centers of the circular paths. The centers of the radiation source assembly 2 and the record carrier 5 respectively, would subtend the same angle φ therewith. The displacement must again be such that a straight line connecting any radiation source to the center of the record carrier 5 will always pass through the same corresponding fixed point (object point) in a corresponding plane through the object for all positions of the radiation source group relative to the stationary object.

In the preceding embodiment the radiation source group 2 must be moved along the circular path so that, in a plan view perpendicular to the radiation source plane 1, each straight line connecting a respective pair of radiation sources will always intersect the coordinate axes x, y (of a flat coordinate system extending parallel to the radiation source plane) at the same angle. The record carrier 5 is similarly displaced along a corresponding circular path.

Obviously, it is again possible to arrange for the radiation source assembly 2 to be stationary and to displace the object 4 or the examination table 3 and the record carrier 5 in the same direction along corresponding circular paths, subject to the constraints described above. Of course, other curved, planar paths, for example elliptical paths, can alternatively be followed. The radiation sources can again be continuously activated or be briefly energized at given points along their path.

Figure 3:
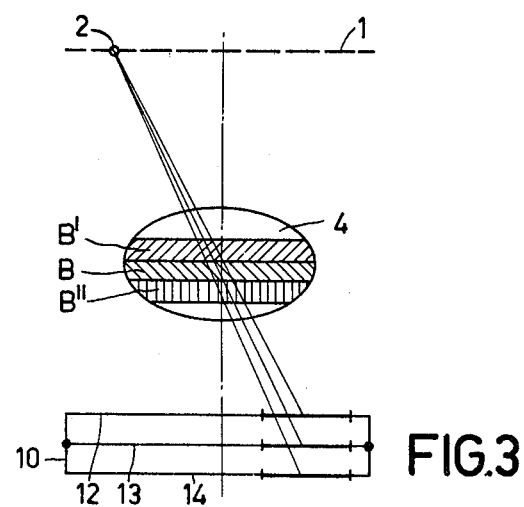
FIG. 3 schematically shows a tomography apparatus according to the invention which comprises a multiple-film cassette for simultaneously forming a plurality of zonographic layer images.

FIG. 3 shows how three layers B', B, B" of the object 4 which are situated one above the other can be simultaneously zonographically recorded by means of a multiple-film cassette 10 in which, for example, three X-ray films 12, 13, and 14 are arranged one above the other at a distance from each other. The layer B' is recorded on the film 12, the layer B on the film 13, and the layer B" on the film 14. The images on the X-ray films 12, 13, 14 represent simultaneous source-distribution encoded images each of which can be employed for the decoding of further layer images which are situated within the respective body layer regions B', B", B''', sharply imaged on the corresponding X-ray film. For the sake of clarity, FIG. 3 shows only one of the sources of the radiation source assembly 2.

What is claimed is:

1. A device for imaging layers of a three-dimensional object, said device comprising:
   radiation source means arranged on first support means on one side of the object to irradiate the object with penetrating radiation from each of a plurality of source positions, said source positions being distributed in a radiation source plane; and a record carrier for recording an encoded composite image of the object, said composite image consisting of a plurality of perspective images, said record carrier being arranged on second support means on a side of the object opposite the radiation source means;

characterized in that the radiation source means and the record carrier are each slidably mounted on their respective support means, said radiation source means and record carrier being constrained to slide in opposite directions in parallel slide planes on opposite sides of the stationary object, said sliding motions being further constrained such that every straight line connecting a radiation source position to the center of the record carrier will always pass through one of a set of fixed points in the object for all positions of the radiation source means, each fixed point being associated with one line originating from a radiation source position, said fixed points being in a single plane in the object; and characterized in that the device further comprises means for sliding the radiation source means and the record carrier.

2. A device as claimed in claim 1, characterized in that the radiation source means and the carrier are slidably mounted on their respective support means such that they can slide only in straight paths.

3. A device as claimed in claim 1, characterized in that the radiation source means and the record carrier are slidably mounted on their respective support means such that they can slide only along curved paths, but without rotating relative to the object around an axis perpendicular to the slide planes.

4. A device as claimed in claim 3, characterized in that the curved paths are circular.

5. A device as claimed in claim 4, characterized in that the record carrier is a multiple-film cassette.

6. A device as claimed in claim 5, characterized in that the object is arranged on an examination table, the radiation source means is arranged above the object, the record carrier is arranged below the object, and the films in the record carrier are stacked one underneath the other.

7. A device for imaging layers of a three-dimensional object, said device comprising:

an examination table on which the object is arranged, said examination table being arranged on first support means;

radiation source means arranged on one side of the object to irradiate the object with penetrating radiation from each of a plurality of source positions, said source positions being distributed in a radiation source plane; and a record carrier for recording an encoded composite image of the object, said composite image consisting of a plurality of perspective images, said record carrier being arranged on second support means on a side of the object opposite the radiation source means;

characterized in that the examination table and the record carrier are each slidably mounted on their respective support means, said examination table and record carrier being constrained to slide in the same direction in parallel slide planes, said sliding motions being further constrained such that every straight line connecting a radiation source position to the center of the record carrier will always pass through one of a set of fixed points in the object for all positions of the object, each fixed point being associated with one line originating from a radiation source position, said fixed points being in a single plane in the object; and characterized in that the device further comprises means for sliding the examination table and record carrier.

8. A device as claimed as claim 7, characterized in that the examination table and the record carrier are slidably mounted on their respective support means such that they can slide only in straight paths.

9. A device as claimed in claim 7, characterized in that the examination table and the record carrier are slidably mounted on their respective support means such that they can slide only along curved paths, but without rotating relative to the radiation source means around an axis perpendicular to the slide planes.

10. A device as claimed in claim 9, characterized in that the curved paths are circular.

11. A device as claimed in claim 7, characterized in that the record carrier is a mutliple-film cassette.

12. A device as claimed in claim 11, characterized in that the radiation source means is arranged above the object, the record carrier is arranged below the object, and the films in the record carrier are stacked one underneath the other.

* * * * *